United States Patent
Minemura et al.

(10) Patent No.: US 6,936,094 B2
(45) Date of Patent: Aug. 30, 2005

(54) ADSORPTIVE SHEET AND FILTER FOR CLARIFYING AIR

(75) Inventors: Shinichi Minemura, Ohtsu (JP); Toyota Seki, Ohta (JP); Makoto Morita, Ohtsu (JP)

(73) Assignee: Toyo Boseki Kabushiki Kaisha, Osaka (JP)

( * ) Notice: Subject to any disclaimer, the term of this patent is extended or adjusted under 35 U.S.C. 154(b) by 68 days.

(21) Appl. No.: 10/490,342

(22) PCT Filed: Sep. 2, 2002

(86) PCT No.: PCT/JP02/08896

§ 371 (c)(1),
(2), (4) Date: Mar. 22, 2004

(87) PCT Pub. No.: WO03/026794

PCT Pub. Date: Apr. 3, 2003

(65) Prior Publication Data

US 2005/0000363 A1 Jan. 6, 2005

(30) Foreign Application Priority Data

Sep. 21, 2001 (JP) .......................................... 2001-289704
Sep. 28, 2001 (JP) .......................................... 2001-302935

(51) Int. Cl.$^7$ ........................... B01D 53/04; B01D 46/10
(52) U.S. Cl. .............................. 96/154; 55/514; 55/524
(58) Field of Search ........................ 96/134, 135, 153, 96/154; 55/385.1, 514, 385.3, 524

(56) References Cited

U.S. PATENT DOCUMENTS

| | | | | |
|---|---|---|---|---|
| 3,484,322 A | * | 12/1969 | Inskeep ....................... 156/292 |
| 3,857,732 A | | 12/1974 | Yoshino |
| 4,160,059 A | * | 7/1979 | Samejima .................... 442/411 |
| 4,289,513 A | * | 9/1981 | Brownhill et al. ............ 96/135 |
| 4,342,811 A | * | 8/1982 | Lopatin et al. .............. 428/220 |
| 4,429,001 A | * | 1/1984 | Kolpin et al. ................ 442/340 |
| 4,433,024 A | * | 2/1984 | Eian ............................. 428/198 |
| 4,510,193 A | * | 4/1985 | Blucher et al. .............. 428/196 |
| 4,699,681 A | * | 10/1987 | Kasmark, Jr. et al. ...... 156/264 |
| 4,992,319 A | * | 2/1991 | Kurosawa et al. ........... 428/116 |
| 5,221,573 A | * | 6/1993 | Baigas, Jr. ................... 428/212 |
| 5,308,703 A | * | 5/1994 | Tsujimoto et al. .......... 428/408 |
| 5,328,758 A | * | 7/1994 | Markell et al. .............. 442/351 |
| 5,338,340 A | * | 8/1994 | Kasmark, Jr. et al. ........ 96/135 |
| 5,486,410 A | * | 1/1996 | Groeger et al. .............. 442/353 |
| 5,662,728 A | * | 9/1997 | Groeger ........................ 96/153 |
| 5,665,148 A | * | 9/1997 | Muhlfeld et al. .............. 96/153 |
| 5,792,513 A | | 8/1998 | Koslow et al. |
| 5,807,424 A | * | 9/1998 | de Ruiter et al. ............. 95/148 |
| 5,869,009 A | * | 2/1999 | Bellefeuille et al. ......... 422/171 |
| 6,024,782 A | * | 2/2000 | Freund et al. ................. 96/154 |
| 6,331,351 B1 | * | 12/2001 | Waters et al. ............. 428/317.7 |
| 2002/0062740 A1 | * | 5/2002 | Brukov et al. ................. 96/153 |

FOREIGN PATENT DOCUMENTS

| | | |
|---|---|---|
| EP | 0 955 087 A1 | 10/1999 |
| JP | 55-42854 | 3/1980 |
| JP | 2000-127274 | 5/2000 |
| JP | 2000-185088 | 7/2000 |
| JP | 2000-312809 | 11/2000 |
| JP | 2001-149730 | 6/2001 |

* cited by examiner

*Primary Examiner*—Robert H. Spitzer
(74) *Attorney, Agent, or Firm*—Morrison & Foerster LLP

(57) ABSTRACT

Provided are an adsorption sheet and an air-purifying filter, which can have low air-flow resistance and high deodorizing performance and be resistant to clogging by dust, from which a powdered adsorbent can hardly drop off, and in which any attached agent can hardly lose its effect. Such a product can be obtained by a process including the steps of: sufficiently premixing an agent-bearing activated carbon powder and a powdered thermoplastic resin to form a mixed powder; then spreading the mixed powder on a base sheet having a certain bulkiness and bearing an agent; stacking an air-permeable sheet thereon; and hot-pressing them.

8 Claims, 1 Drawing Sheet

ADSORPTIVE SHEET AND FILTER FOR CLARIFYING AIR

TECHNICAL FIELD

The invention relates to an adsorption sheet having a deodorizing function and to an air-purifying filter having a dust-removing function and a deodorizing function.

BACKGROUND ART

A typical technique of applying an adsorbent to an air-purifying filter includes the methods of producing an adsorbent-containing sheet and then placing the surface of the sheet perpendicular to the flow of the air to be purified. However, practically no conventional filter fully satisfies the important characteristics with respect to air-flow resistance, adsorption characteristics or dust-removing performance. Although there are a variety of conventional techniques lowering the air-flow resistance, no manufacturing method is practical, particularly because the conventional method tends to be complex.

Japanese Patent Application Laid-Open No.10-99421 discloses a method of producing an adsorption sheet using adsorbent particles and a powdered thermoplastic resin, which includes the steps of mixing the powdered thermoplastic resin of 100 to 1000 μm and granular activated carbon and then spreading the mixture on a base sheet and fixing it by pressing. This method uses a relatively large powdered thermoplastic resin and thus has the problem that a large amount of the powdered thermoplastic resin is needed for a sufficient adhesive effect so that the air-flow resistance can be high. The method also has the problem that the powdered thermoplastic resin can be fused to form a film in the vicinity of the boundary between the base sheet, the activated carbon and the thermoplastic resin in the mixture so that the air-flow resistance can be higher.

Japanese Patent Application National Publication (Laid-Open) No.07-509656 (with no description of the base sheet-combined type adsorption sheet) discloses a method for reducing the air-flow resistance of a molded activated carbon product, which includes the steps of: preheating adsorbent particles to a temperature higher than the melting range of a powdered thermoplastic resin; then mixing the heated adsorbent particles and the powdered thermoplastic resin to form fine agglomerates of at least 15 mesh; using a screen to select specific agglomerates; molding the agglomerates into the desired open-shaped flat structure; heating the flat structure to a temperature higher than the melting range of the powdered thermoplastic resin; and then cooling it. According to the disclosure, the two separate heating steps before and after the mixing step are needed for the production of the agglomerates. Such steps are required to consume considerable amounts of energy and time, and for example, each step takes as much as 40 minutes. It is also suggested that the melt of the powdered thermoplastic resin can be compressed by the influence of their own weight of the agglomerates so that the product can fail to have good permeability and that a well-permeable product cannot be obtained without an improved process including the step of turning the molded product upside down during the step of fusing the powdered thermoplastic resin.

JP-A No.08-290055 discloses a method for reducing the time of manufacturing a low air-flow resistance adsorption sheet, which includes the steps of adding 15 to 70% by weight of water to a mixture of activated carbon and a powdered thermoplastic resin so that the binding between the activated carbon particles is weakened by steam generated in a hot pressing process and performing a continuous process to form a product with a reduced air-flow resistance. In the end, the step of producing a final dry sheet requires considerable amounts of heat energy for evaporating the water, and such a method can be high in manufacturing cost and cannot be so practical.

In terms of deodorizing performance, odor gases and poisonous gases are broadly grouped under neutral, acidic and basic gases. A non-polar adsorbent such as activated carbon can have enough ability to adsorb the neutral gas by physical adsorption activity but cannot be so effective in adsorbing the acidic or basic gas as it is. Thus, the activated carbon should be treated with an agent for increasing the acidic or basic gas-adsorbing effect.

Japanese Utility Model Application Laid-Open No.04-41718 discloses a method including the step of attaching an organic acid and an amine compound to an activated carbon-bearing sheet substrate, wherein the attached organic acid can enhance the effect of removing ammonia and gaseous amines and the attached amine compound can enhance the effect of removing aldehydes, hydrogen sulfide, mercaptan, and the like. In this method, the two agents, the acid and the base, can be brought in contact and react with each other to lose their activity, so that the originally designed level of the deodorizing performance cannot fully be attained.

JP-A No.06-39238 discloses an improved method on the problems, which includes the step of using a water-soluble binder to increase the viscosity of the solution and to separate the acidic gas-adsorbent attached to an activated carbon sheet from the alkaline gas-adsorbent attached to an air-permeable sheet, wherein the activated carbon sheet and the air-permeable sheet are combined to form a single adsorption sheet. In this method, the attachment of the acidic gas-adsorbent to a more inner part of the activated carbon sheet can cause contact of the acidic gas-adsorbent with the air-permeable sheet to which the alkaline gas-adsorbent is attached, so that the adsorbents can lose their activity.

JP-A No.2000-84339 discloses a method including the steps of sandwiching a mixed powder of an activated carbon particle layer and a powdered thermoplastic resin between two air-permeable sheets having a deodorizing function and then hot-pressing them. In this method, the powdered thermoplastic resin has a large size of 50 to 2000 μm. Such large resin particles can increase the direct contact area between the activated carbon and the air-permeable deodorant sheet. In a case where a certain chemical is attached to the activated carbon, therefore, the chemical-bearing activated carbon and the air-permeable deodorant sheet can interfere with each other so that the deactivation rate can increase. In addition, the surface of the chemical-bearing activated carbon cannot uniformly hold the powdered thermoplastic resin. In a case where different chemicals are attached to the activated carbon, therefore, they can interfere with each other so that the deactivation rate can also increase.

JP-A No.11-57467 discloses an adsorption sheet with an improvement on the above problems, which comprises:

a plurality of laminated units each comprising deodorant powder; and a web comprising a connecting portion made of a hot-melt resin and an agglomerate resin portion, wherein the deodorant powder of the one laminated unit is fixed on one surface of the web via the agglomerate resin portion;

the deodorant powder of the another laminated unit is fixed on the other surface of the web via the agglomerate resin portion;

the adsorption sheet is a laminate type deodorant filter having at least two types of the deodorant powders; each laminated unit has only one type of the deodorant powder; and the units are laminated and integrated into a single piece. In this technique, however, the different types of the deodorant powders must be used for the different laminated units, so that the sheet having at least two different types of the deodorant powders must be thick. According to this technique, a pleated or corrugated filter unit formed of such a sheet cannot have a large number of ridges and cannot exhibit satisfactory performance.

In order to solve the above problems, the inventors have made active investigations on the base sheet for use, the powdered thermoplastic resin for use and manufacturing conditions and consequently have found a method that can produce, at low cost, an adsorption sheet with very low air-flow resistance, good deodorizing performance and good dust-removing performance. Also provided is an adsorption sheet that can offer its performance more effectively without interference between two or more agents even in a case where the two or more types of the agents are attached to a powdered adsorbent or in a case where the agents are attached to a base sheet and an air-permeable sheet.

SUMMARY OF INVENTION

Thus, the invention is directed to:

an adsorption sheet, comprising a structure formed by a process including the steps of:

spreading a mixed powder on a base sheet, wherein the mixed powder is a product of sufficiently premixing a powdered adsorbent and a powdered thermoplastic resin having a melt index of 0.1 to 80 g/10 minutes; and then pressing the mixed powder-containing base sheet at a temperature equal to or higher than a melting point of the powdered thermoplastic resin to form the adsorption sheet, wherein the base sheet has a fiber packing density of 0.15 g/cc or less;

the adsorption sheet, wherein the powdered thermoplastic resin has an average particle diameter of 1 to 40 $\mu$m;

the adsorption sheet, wherein the mixed powder has a weight ratio of the powdered thermoplastic resin to the powdered adsorbent of 1 to 40% by weight;

the adsorption sheet, wherein in a dust supply test using a JIS powder type No.15, the adsorption sheet with the base sheet surface facing upstream holds 30 g/m$^2$ or more of the powder by the time when its air-flow resistance increases from the initial value by 150 Pa under the conditions of a linear velocity of 30 cm/second and a dust concentration of 0.5 g/m$^3$;

the adsorption sheet, wherein an agent is held on the powdered adsorbent, and another different agent is held on the base sheet and/or an air-permeable sheet;

the adsorption sheet, wherein the powdered thermoplastic resin is made of at least one selected from polyolefins, polyamides, polyurethanes, polyesters, an ethylene-acryl copolymer, polyacrylate, polyarene, polyacryl, polydiene, an ethylene-vinyl acetate copolymer, PVC, and PS and the like.

a laminate structure, comprising: any of the above adsorption sheets having the mixed powder of the powdered adsorbent and the powdered thermoplastic resin; and a laminated air-permeable sheet, wherein the mixed powder is placed between the base sheet and the air-permeable sheet; and an air-purifying filter comprising the above laminate structure.

DETAILED DESCRIPTION OF THE INVENTION

The invention is described in detail below.

In the invention, the powdered thermoplastic resin serves to bond the powdered adsorbent together and to bond the powdered adsorbent and the base sheet or to bond the powdered adsorbent and the air-permeable sheet.

Examples of the type of the powdered thermoplastic resin include polyolefins, polyamides, polyurethanes, polyesters, an ethylene-acryl copolymer, polyacrylate, polyarene, polyacryl, polydiene, an ethylene-vinyl acetate copolymer, PVC, and PS. Polyolefins and an ethylene-acryl copolymer are preferred, and the ethylene-acryl copolymer is more preferred, because of its excellent adhesion and dispersion properties.

The powdered thermoplastic resin preferably has an average size of 1 to 40 $\mu$m, more preferably of 5 to 30 $\mu$m. In a still more preferred manner, the size of at least 95% by weight of the resin is within the range from 1 to 40 $\mu$m. If the average size is smaller than 1 $\mu$m, the resin can tend to block surface pores of the powdered adsorbent so that the adsorption performance can significantly be reduced. If the average size is larger than 40 $\mu$m, the pre-adhesion of the resin to the powdered adsorbent by Van der Waals force or electrostatic force can partially be weak during the mixing step, so that non-uniform adhesion can occur in the finally heat-treated adsorption sheet and that good quality can be difficult to obtain. If the resin is relatively smaller than the powdered adsorbent, the resin can easily mingle with the powdered adsorbent in a dry state by electrostatic force and Van der Waals force during the mixing step, so that the resulting sheet can be more uniform in properties. The shape of the resin is not particularly defined, and for example, may be spherical, crushed, or the like. As a matter of course, two or more types of powdered thermoplastic resins may be used in combination. Even in a case where an agent-bearing powdered adsorbent or an agent-bearing base sheet or air-permeable sheet is used, the powdered thermoplastic resin in the above manner can temporarily adhere to the surface of the powdered adsorbent during the mixing step in a dry state. Thus, the agents different in property can also be prevented from interfering with each other in the later sheet-forming step, so that sufficient effects can be achieved. Of course, two or more types of powdered thermoplastic resins may be used in combination, or the powdered adsorbent holding two or more types of agents may be applied to a single sheet.

The melting point of the powdered thermoplastic resin is preferably 80° C. or higher in terms of the ambient temperature of a room such as a vehicle room and the like. The melting point is more preferably 100° C. or higher.

As regards the fluidity of the melt of the powdered thermoplastic resin, the MI value of the resin according to JIS K 7210 is preferably from 1 to 80 g/10 minutes, more preferably from 3 to 30 g/10 minutes. If the MI value is too large, the resin can have high fluidity on the surface of the adsorbent so that it can flow and extend over the surface of the adsorbent to block surface pores and that effective deodorizing performance cannot be obtained. If the MI value is too small, it can be difficult to obtain the desired adhesion, and the process should need a large amount of energy for melting and therefore cannot be advantageous in terms of manufacturing cost.

The content of the powdered thermoplastic resin based on the amount of the powdered adsorbent is preferably from 1 to 40% by weight, in view of the adhesion, air-flow resistance and deodorizing performance. The content is more preferably from 5 to 30% by weight.

For example, the particle size of the powdered thermoplastic resin is adjusted by mechanical pulverization, freeze pulverization, chemical method, or the like. Finally, the powdered resin may be screened to a specific particle size, but any method may be used as long as it can ensure a specific particle size.

In the invention, the packing density of the fiber component in the base sheet is preferably 0.15 g/cc or less, more preferably 0.10 g/cc or less. It is because the base sheet with a somewhat low packing density can advantageously form an adsorption sheet with low air-flow resistance and high dust holding capacity by the process including the steps of: spreading, on the base sheet, the mixed powder of the powdered adsorbent and the powdered thermoplastic resin; and then hot-pressing them to form the adsorption sheet. In addition, crimped fibers are more preferably used, because they can allow the mixed powder to stay in a loose manner.

Any method may be used without limitation to produce the base sheet. For example, the base sheet may be produced by a method including the steps of using a nonwoven short- or long-fiber fabric or a woven fabric and subjecting it to embossing or needle-punching, integrating it with a reinforcing sheet or impregnating it with a binder resin. In such a process, the nonwoven or woven fabric should have certain strength so as not to be broken under a certain tension.

The distance between the fibers in the vicinity of the mixed powder-receiving surface of the base sheet should be 10 $\mu$m or more, preferably 40 $\mu$m or more. If the distance is less than 10 $\mu$m, the density of the powdered thermoplastic resin can be high in the vicinity of the sheet surface after the step of spreading the mixed powder, so that the sheet can tend to have a high air-flow resistance after heat treatment. It is also important that the distance between the fibers is not too longer than the particle size of the mixed powder in terms of preventing the mixed powder from dropping off from the opposite surface of the base sheet. The distance between the fibers in the vicinity of the mixed powder-receiving surface may be determined by observation using an optical or electron microscope.

The powdered thermoplastic resin adheres on the surface of the mixed powder and thus can effectively be used for adhesion to the base sheet.

Any material may be used for the base sheet-forming fiber, such as polyolefins, rayons, polyesters, polyamides, polyurethanes, polyacryls, polyvinyl alcohols, and polycarbonate. Of course, sheath-core type fibers or a fiber blend of different fibers may also be used. An electrostatically-charged nonwoven fabric, a so-called electret sheet may also be used for the base material. Such a fabric can increase the effect of arresting submicron particles such as cigarette smoke particles, carbon particles and marine salt particles. In any case, the melting point of the fiber should be higher than the sheet-heating temperature for use in melting the powdered thermoplastic resin. In the sheath-core type fiber, therefore, the core fiber should have a higher melting point.

The constitutional components may be the base sheet and the mixed powder of activated carbon and the powdered thermoplastic resin. For better handling ability, an air-permeable sheet may be laminated on the adsorbent-releasing side, namely the opposite side of the base sheet. The powdered thermoplastic resin adheres to the surface of the activated carbon and thus can effectively be used for adhesion to the air-permeable sheet. The air-permeable sheet may be similar to the base sheet. However, a relatively thin air-permeable sheet is preferably used, because such a thin sheet can contribute to a reduction in fold pitch, an increase in the area of the adsorption sheet, a reduction in air-flow resistance, or an improvement in the deodorizing performance, in a case where the adsorption sheet is pleated or corrugated for use as an air-purifying filter unit. The whole thickness is preferably from about 0.3 to about 2.5 mm.

An alternative method may include the steps of: stacking, on the base sheet, any other bulky sheet in which the distance between the fibers is larger than the powdered adsorbent for use; and then spreading the mixed powder from above the bulky sheet. This method can suppress excessive agglomeration or cohesion of the adsorbent particles and can make the binding state between the adsorbent particles looser, so that the air-flow resistance can further be reduced.

In view of air permeability, dropping off of the adsorbent, workability of the sheet, and the like, the average particle diameter of the adsorbent for use in the inventive adsorption sheet is preferably from 60 to 800 $\mu$m, more preferably from 100 to 600 $\mu$m, according to the value obtained by the JIS standard screen (JIS Z 8801). If the average particle diameter is less than 60 $\mu$m, the air-flow resistance can be too high when a specific high adsorption capacity is obtained. At the same time, the packing density of the sheet can tend to be high, and such a small adsorbent can cause a rise in air-flow resistance at an early stage of the dust supply. If the average particle diameter is more than 800 $\mu$m, the adsorbent can easily drop off, and the initial adsorption performance by one pass can be extremely low. In such a case, the workability can also be low when the sheet is folded or corrugated into a pleated or corrugated filter unit for air purification. The powdered adsorbent can be obtained after particle size regulation using a conventional classifier.

The powdered adsorbent for use in the inventive adsorption sheet may be in the form of a powder, a granule, a pulverized product, granulated product or beads, and is preferably an activated carbon-based material, which is capable of adsorbing a wide variety of gases. Preferred examples of the activated carbon include that from coconut shell, that from wood, that from coal, and that from pitch. The number of pores for introducing substances into the inside, so-called macropores, observed in the surface, is preferably as large as possible. When the powdered mixture is produced from the activated carbon and the powdered thermoplastic resin, the surface of the activated carbon may be coated with the thermoplastic resin. In such a case, however, the adsorbing pores can be opened by desorption of gases from the interior of the pores during the hot pressing process. The activated carbon should have a somewhat rough surface, because such a surface can reduce the fluidity of the resin melt and thus can suppress the decrease in adsorption performance.

According to JIS K 1474, the amount of toluene adsorbed by the powdered adsorbent for use in the inventive adsorption sheet is preferably 20% by weight or more. This is because high adsorption performance should be required for adsorption of nonpolar gaseous substances such as offensive odor gases and adsorption of nonpolar liquid substances.

The adsorbent for use in the inventive adsorption sheet may be treated with an agent so as to show improved adsorption of polar substances or aldehydes.

Preferred examples of such an agent for use in the treatment of gaseous chemicals, specifically in the treatment of aldehyde gases, nitrogen compounds such as $NO_x$, sulfur compounds such as $SO_x$, or acidic polar substances such as acetic acid, include amine agents such as ethanolamine, polyethyleneimine, aniline, p-anisidine, and sulfanilic acid; sodium hydroxide, potassium hydroxide, guanidine carbonate, guanidine phosphate, aminoguanidine sulfate, 5,5-dimethylhidantoin, benzoguanamine, 2,2-iminodiethanol, 2,2,2-nitrotriethanol, ethanolamine hydrochloride, 2-aminoethanol, 2,2-iminodiethanol hydrochloride, p-aminobenzoic acid, sodium sulfanilate, L-arginin, methylamine hydrochloride, semicarbazide hydrochloride, hydrazine, hydroquinone, hydroxylamine sulfate, permanganate, potassium carbonate, and potassium hydrogencarbonate. Preferred examples of such an agent for use in the treatment of basic polar substances such as ammonia, methylamine, trimethylamine, and pyridine include phosphoric acid, citric acid, malic acid, ascorbic acid, and tartaric acid. For example, the agent treatment is performed by adding or attaching the agent to the activated carbon. A method of attaching the agent to the vicinity of the surface of the sheet by a conventional coating process or a method of impregnating the whole of the sheet with the agent may also be used as an alternative to the method of directly treating the activated carbon with the agent. In such a method, an aqueous solution of the agent, which contains a thickener such as sodium alginate and polyethylene oxide, may be prepared and added or attached. Such a method is effective at adding or attaching an agent with a low solubility in water and effective at suppressing the dropping off of the agent.

The inventive adsorption sheet may contain a component having an optional function, such as an antibacterial agent, an antifungal agent, an antiviral agent, and a flame retardant. Such a component may be mingled into fibers or a non-woven or woven fabric, or may be added or attached in a later process. For example, the flame retardant may be added to form an adsorption sheet satisfying the standards for flame retardation according to FMVSS.302 or the UL flame-retardant standards.

The component having the optional function may be added or attached to the activated carbon. In such a case, it should be noted that the original adsorption function of the activated carbon should not be reduced. The fibers of the base sheet, the air-permeable sheet or the like may also have the adsorption function. In order to strengthen the deodorizing function, for example, an acid or an alkali may be added or attached to the fibers, or ion-exchange fibers may be used.

A description is provided below of a basic method of manufacturing the adsorption sheet. Predetermined weights of the powdered adsorbent and the powdered thermoplastic resin are weighed and added to a shaker (a stirrer) to be stirred at a rotational speed of 30 rpm for about 10 minutes. During this step, the moisture percentage is preferably 15% or less based on the weight of the mixture. At this time, the powdered thermoplastic resin is temporarily bonded to the surface of the powdered adsorbent to form a mixture. The resulting mixed powder is then spread on the base sheet and subjected to a hot pressing treatment, in which the surface of the sheet has a temperature about 3 to 30° C. higher, preferably about 5 to 20° C. higher than the melting point of the powdered thermoplastic resin. In this process, the air-permeable sheet may also be laminated so as to form an easier handling adsorption sheet.

Before the heat treatment, the mixed powder may be preheated and temporarily bonded by infrared radiation or the like, so that random flow of the mixed powder can be prevented, which otherwise could easily occur in the press step, and that the powder dispersion can further be improved in the resulting adsorption sheet. In the heat treatment with the infrared radiation, which can be free of air current, the mixed powder can remain at rest and can be prevented from flying off.

Examples of the method of forming a sheet by hot pressing include a popular hot roll pressing method in which the hot pressing is performed between rolls and a flat bed laminating method in which the material is sandwiched between upper and lower flat hot conveyor belts. The latter method is more preferred for the purpose of making thickness and adhesion state more uniform. The combination of the base sheet according to the invention and the features of the above manufacturing method can suppress excessive binding between the adsorbent particles, so that in the vicinity of the base sheet, the packing density of the powdered adsorbent can be 5 to 30% lower than that in the case where the active carbon is only used. Thus, low air-flow resistance and high dust holding capacity can be achieved. The dust holding capacity of the sheet is preferably 30 $g/m^2$ or more (the method of measurement is described in the examples below). If the dust holding capacity of the sheet is less than 30 $g/m^2$, the sheet can be clogged at an early stage of use, the pressure loss can rise early, and it can be a cause of practical problems. For example, a filter to be installed in one piece of a car air conditioner has a size of 200 mm long×200 mm wide×20 mm ridge-high, a ridge-to-ridge pleat pitch of 5 mm and a filter area of about 0.32 $m^2$. To be used effectively for a year under a load of JIS dust type No. 15, such a filter must hold 10 g of the dust per piece. If the filter has a dust holding capacity of 30 $g/m^2$ or more, therefore, it can effectively be used for one year or more.

Two pieces of base sheets on which the mixed powder of the powdered adsorbent and the powdered thermoplastic resin is spread may be laminated in such a manner that the surface of each base sheet faces outside. It can have a high loading of activated carbon and a low air-flow resistance and can provide a high dust-holding capacity for the adsorption sheet. Such a method is described in detail in the examples below.

The air-purifying filter of the invention preferably has a thickness of 10 to 400 mm. The filter for use in a vehicle including the filter to be installed in a car air conditioner or the filter for use in a home air cleaner preferably has a thickness of about 10 to 60 mm in terms of usual interior space. A large filter unit frequently used for air conditioning of buildings preferably has a thickness of about 40 to 400 mm in terms of housing space.

In the pleated air-purifying filter of the invention, the distance between the adjacent ridges (ridge-to-ridge pleat pitch) is preferably from 2 to 30 mm. If the pitch is less than 2 mm, the ridges located too close to each other can form a lot of dead space, and thus the sheet cannot efficiently be used. If the pitch is more than 30 mm, the developed area of the sheet can be relatively small so that the resulting removal effect cannot correspond to the thickness of the filter.

Either surface of the inventive air-purifying filter may be placed upstream during use. In a case where a bulky base sheet is used, however, it is preferred that the base sheet be placed upstream during use. It is because in such a case, the dust holding capacity by the time when the air-flow resistance reaches a certain final value can practically be higher, namely it can be resistant to clogging.

Figure 1:
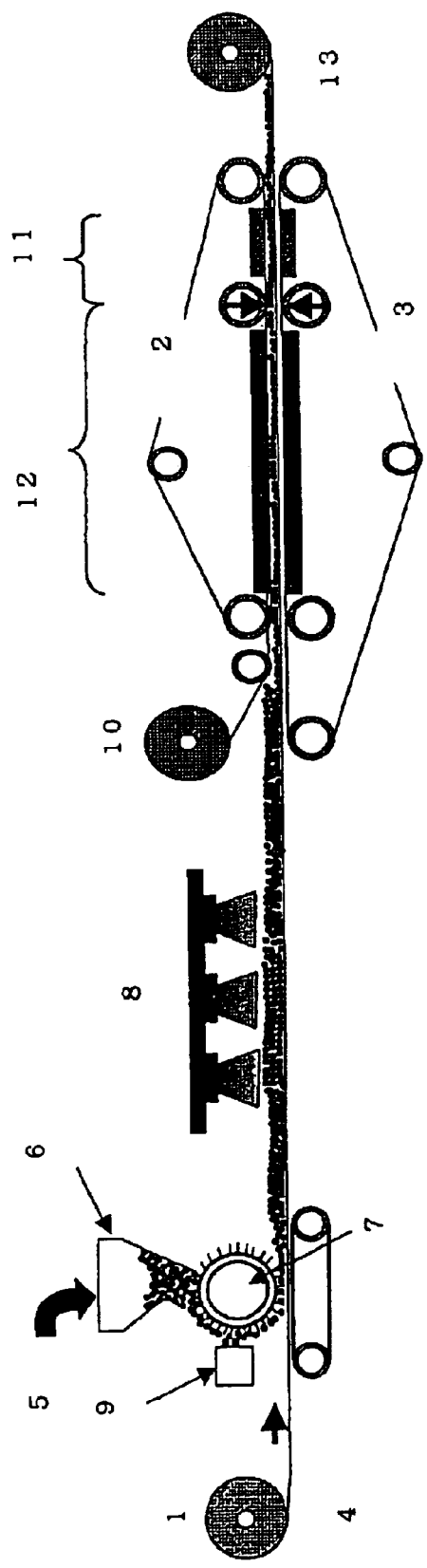
FIG. 1 is a schematic diagram showing an example of the apparatus system for manufacturing the inventive adsorption sheet by flat bed laminating method.
Figure 2:
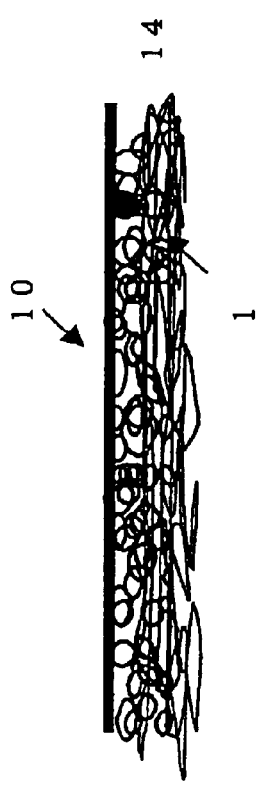
FIG. 2 is a schematic diagram of the inventive adsorption sheet.

In the drawings, reference numeral 1 represents a base sheet, 2 or 3 a belt conveyor, 4 an unwinder, 5 a mixed powder, 6 a hopper, 7 a powder vibrating spreader, 8 a preheater, 9 a projecting needle, 10 an air-permeable sheet, 11 a cooling zone, 12 a hot pressing zone, 13 a winder, and 14 a mixed powder of a powdered adsorbent and a powdered thermoplastic resin, respectively.

BEST MODE FOR CARRYING OUT THE INVENTION

The invention is further described in detail in the examples below, which are not intended to limit the scope of the invention. It will also be understood that any modifications according to the description above or below should be included in the technical scope of the invention.

<Measurement Methods>

The numerical values in the examples below were measured by the methods below.

(1) Thickness

The thickness value was measured under a load pressure of 180 gf/cm$^2$.

(2) JIS Dust Type No. 15*-Holding Capacity (measured under the conditions of a linear velocity of 30 cm/s and a dust supply concentration of 0.5 g/m$^3$)

This value represents a clogging degree to dust. Under the above conditions, the time when the air-flow resistance increased from the initial value by 150 Pa was determined as the end of the life. At that time, the amount of the dust deposited on the filter was weighed using a balance, and the resulting weight value was used as the dust holding capacity. The measurement was performed using a sample of a size of 15 cm×15 cm.

*: JIS dust type No. 15 is a mixed powder of the following components:
JIS dust type No.8 (with an average size of about 8 $\mu$m, Kanto-loam) 72%
Carbon black (with an average size of about 0.1 $\mu$m) 23%
Cotton linter (with an average size of about 1.5 $\mu$m) 5%

(3) The air-flow resistance is a value measured at a linear velocity of 30 cm/s. The measurement was performed using a cut sample of 70$\phi$.

(4) Deodorizing Performance (i) Measurement of Physical Adsorption Performance

Toluene gas was used at a linear velocity of 30 cm/s, and its concentrations upstream and downstream from the filter were each measured with a Gastech detector tube. The downstream gas concentration was subtracted from the upstream gas concentration, and the resulting value was divided by the upstream gas concentration and converted to a percentage value. The measurement was performed using a cut sample of 6 cm×6 cm. In the examples, the upstream concentration was 80 ppm, and the removal rate data as shown in the examples were obtained one minute after the start of the measurement.

(ii) Measurement of Aldehyde Gas Adsorption Performance

Acetaldehyde was used at a linear velocity of 30 cm/s, and its concentrations upstream and downstream from the filter were each measured with a Gastech detector tube. The downstream gas concentration was subtracted from the upstream gas concentration, and the resulting value was divided by the upstream gas concentration and converted to a percentage value. The measurement was performed using a cut sample of 6 cm×6 cm. In the examples, the upstream concentration was 3 ppm, and the removal rate data as shown in the examples were obtained one minute after the start of the measurement.

(iii) Measurement of Basic Gas Adsorption Performance

Ammonia was used at a linear velocity of 30 cm/s, and its concentrations upstream and downstream from the filter were each measured with a Gastech detector tube. The downstream gas concentration was subtracted from the upstream gas concentration, and the resulting value was divided by the upstream gas concentration and converted to a percentage value. The measurement was performed using a cut sample of 6 cm×6 cm. In the examples, the upstream concentration was 30 ppm, and the removal rate data as shown in the examples were obtained one minute after the start of the measurement.

(5) Sheet Packing Density, Bulk Density Sheet packing density (g/cc)=(weight per unit area of sheet)/(thickness of sheet)

(The thickness of the sheet is a value under a load of 180 gf/cm$^2$.)

At a linear velocity of 30 cm/s, a comparison was made on peeling of the base sheet and the air-permeable sheet.

Specific examples are shown below. In the examples, Sheet A, Sheet A1 and Sheet B each have the composition as shown below.

Sheet A: Polyester fibers of 1.8 dtex×51 mm and 2.7 dtex×51 mm were mixed in a weight ratio of 1:1 in a card and then impregnated with an acrylic resin and dried to form a relatively strong sheet. The resulting sheet had a weight per unit area of 30 g/m$^2$ (fiber: 20 g/m$^2$, acrylic resin load: 10 g/m$^2$), a thickness of 0.3 mm, and a fiber packing density of 0.67 g/cc. In the sheet, the fibers are entirely crimped. When observed with a microscope, the distance between the fibers in the surface of the sheet is at least 40 $\mu$m. The sheet has an air-flow resistance of 3 Pa.

Sheet A1: Sheet A was subjected to a usual dipping process in an aqueous solution of 10 parts by weight of citric acid and 90 parts by weight of water, so that the acid was attached to the whole of the sheet. The water was squeezed from the sheet through a mangle, and the sheet was continuously dried at 100° C. in a cylindrical drier. The resulting sheet had a weight per unit area of 40 g/m$^2$ (fiber: 30 g/m$^2$, acrylic resin load: 10 g/m$^2$, citric acid: 10 g/m$^2$). On the other hand, the sheet was the same as Sheet A with respect to thickness, fiber packing density, distance between fibers in the sheet surface, and air-flow resistance.

Sheet B: Polyolefin-based spunbond nonwoven fabric (Eleves T0203 (trade name) manufactured by Unitika Ltd.) with a weight per unit area of 20 g/m$^2$, a thickness of 0.11 mm, a packing density of 0.18 g/cc, and an air-flow resistance of 5 Pa.

EXAMPLE 1

Weighed were 1 kg of granular activated carbon from coal (with an average particle diameter of 300 $\mu$m and a toluene adsorption ability of 47% by weight measured according to JIS K 1474) and 0.1 kg of a powdered thermoplastic resin (Flo-Beads EA209 manufactured by Sumitomo Seika Chemicals Co., Ltd. (an ethylene-acrylic acid copolymer material with an average particle diameter of 10 $\mu$m, an MI value of 9 g/10 minutes and a melting point of 105° C.)), and stirred and mixed in a small hoop shaker (Kyomachi Ltd.) at 20 rpm for about 10 minutes. In the resulting mixed powder taken out of the container, the resin was held on the surface of the activated carbon to give a whitish appearance. At this time, the whole moisture content was 8% by weight. Sheet A was used as the base sheet, on which the resulting mixed powder was spread at a density of 240 g/m$^2$. Sheet B was then superposed over the base sheet and subjected to hot pressing, cooling and winding, so that the desired adsorption sheet was obtained. The spreading and the heating process are further described in detail below. FIG. 1 is a schematic diagram showing a flat bed laminating method for manufacturing the adsorption sheet of the invention. The equipment includes upper and lower belt conveyors 2 and 3, which are each coated with a fluororesin and provided for conveying a base sheet 1 (Sheet A in this example). The mixed powder 5, a product of premixing the activated carbon and the powdered thermoplastic resin, was introduced into a hopper 6. The base sheet 1 was then unwound from an unwinder 4, and the mixed powder 5 was spread on the base sheet 1 from a powder vibrating spreader 7, which was provided for spreading the mixed powder 5 at a substantially uniform density from the hopper 6. The rotating powder vibrating spreader 7 vibrates and spreads the mixed powder 5 from the hopper 6 with the aid of a large number of projecting needles 9, which are attached to the surface of a cylindrical member provided below in the perpendicular direction. In such a structure, the mixed powder 5 can be spread at a substantially uniform density. The sheet was then placed between the conveyor belts in a hot pressing zone 12 with about 3 m long in which the surface temperatures of the upper and lower belts were each set at 120° C. The clearance between the belts is required to be smaller than the finally completed adsorption sheet, in order that the sheet should be produced with constant quality. Thus, the clearance was set at 0.6 mm in this process. It has been found that in such a process, if a preheater 8 for preheating with infrared radiation is operated so as to heat the material at 120° C. slightly higher than the melting point of the powdered thermoplastic resin before the step of inserting the sheet between the conveyor belts, the possibility of causing a random flow of the mixed powder can further be reduced so that fluctuations in thickness, air-flow resistance and the like can be reduced; otherwise such a random flow could easily occur in the step of inserting the sheet between the conveyors. The sheet was then allowed to pass through a cooling zone 11 so that the powdered thermoplastic resin was stabilized, and the sheet was wound on a winder 13. The process was performed at a line speed of 10 m/minutes. In addition, an air-permeable sheet 10 (Sheet B in this example) was inserted from above immediately before inserted between the conveyor belts, so that another integrated sheet was obtained in which the mixed powder of the activated carbon and the powdered thermoplastic resin was sandwiched between both sheets. The combination of Base Sheet A described above and the features of the above manufacturing method was able to suppress excessive binding between the activated carbon particles, and in the vicinity of the base sheet, the packing density of the activated carbon was about 20% lower than that in the case where the active carbon was only used. Thus, a low air-flow resistance and a high dust holding capacity were attained. In the table below, data on the sandwich type sheet with air-permeable Sheet B are shown for comparison. It is apparent from the data that the resulting adsorption sheet is thin, and has good adhesion properties, a low air-flow resistance, a high dust holding capacity, and a high deodorizing performance, and therefore should be ideal.

Comparative Example 1

An adsorption sheet was produced using the sheet composition and the process of Example 1, except that the activated carbon and the powdered thermoplastic resin were not sufficiently mixed in advance and that the insufficiently mixed powder was introduced into the hopper 6. The resulting sheet had poor adhesion properties, and the other resulting characteristics were not satisfactory.

Comparative Example 2

An adsorption sheet was produced using the process of Example 1, except that Sheet B which is a less bulky sheet was used as the base sheet. The resulting air-flow resistance and dust holding capacity were not satisfactory.

EXAMPLE 2

An adsorption sheet was prepared using the process of Example 1, except that the powdered thermoplastic resin used was Flo-Beads LE2080 manufactured by Sumitomo Seika Chemicals Co., Ltd. (a low-density polyethylene material with an average particle diameter of 12 $\mu$m, an MI value of 70 g/10 minutes and a melting point of 105° C.). A good result was obtained.

EXAMPLE 3

An adsorption sheet was prepared using the process of Example 1, except that the powdered thermoplastic resin used was Petrothene 202 manufactured by Tosoh Corporation (a low-density polyethylene material with an average particle diameter of 30 $\mu$m, an MI value of 24 g/10 minutes and a melting point of 106° C.). A good result was obtained.

EXAMPLE 4

An adsorption sheet was prepared using the process of Example 1, except that the powdered thermoplastic resin used was Flo-Beads HE3040 manufactured by Sumitomo Seika Chemicals Co., Ltd. (a high-density polyethylene material with an average particle diameter of 12 $\mu$m, an MI value of 40 g/10 minutes and a melting point of 130° C.) and that the temperatures of the upper and lower conveyor belts were each set at 140° C. during hot pressing. A good result was obtained.

EXAMPLE 5

An adsorption sheet was prepared using the process of Example 1, except that the powdered thermoplastic resin used was a freeze ground product of GM 900 manufactured by Toyobo Co., Ltd. (a polyester material with an average particle diameter of 35 $\mu$m, an MI value of 78 g/10 minutes and a melting point of 115° C.) and that the temperatures of the upper and lower conveyor belts were each set at 130° C. during hot pressing. A good result was obtained.

EXAMPLE 6

The process of Example 1 was used, except that the spread amount of the mixed powder was about half, 132 g/m$^2$ and that the clearance between the upper and lower conveyor belts was accordingly reduced to 0.4 mm. The resulting adsorption sheet had satisfactory characteristics.

EXAMPLE 7

The process of Example 1 was used, except that the activate carbon used had a larger particle size, the spread amount of the mixed powder was about double, 484 g/m$^2$, and the clearance between the upper and lower conveyor belts was accordingly increased to 1.1 mm. The resulting adsorption sheet had satisfactory characteristics.

EXAMPLE 8

Weighed were 1 kg of polyethyleneimine-bearing activated carbon, which was prepared by a process including the steps of adding 10% by weight of Polyethyleneimine SP006 manufactured by Nippon Shokubai Co., Ltd. to granular activated carbon from coal and drying the mixture (which had an average particle diameter of 300 μm and a toluene adsorption ability of 35% by weight measured according to JIS K 1474) and 0.1 kg of a powdered thermoplastic resin (Flo-Beads EA209 manufactured by Sumitomo Seika Chemicals Co., Ltd. (an ethylene-acrylic acid copolymer material with an average particle diameter of 10 μm, an MI value of 9 g/10 minutes and a melting point of 105° C.)), and stirred and mixed in a small hoop shaker (Kyomachi Ltd.) at 20 rpm for about 10 minutes. An adsorption sheet was prepared using the process of Example 1, except that the above agent-bearing activated carbon was used and that Sheet A1 was used as the base sheet.

It has been demonstrated that the resulting sheet has a high air-flow resistance and a high dust holding capacity and shows a high removal rate with respect to each of the three types of gases.

EXAMPLE 9

The formulation of Example 1 was used, except that two types of agent-bearing activated carbons were mixed as shown below. A first mixed powder was prepared by sufficiently mixing EA209 and 10% by weight polyethyleneimine-bearing dry granular activated carbon from coal (with an average particle diameter of 300 μm and a toluene adsorption ability of 35% by weight measured according to JIS K 1474). A second mixed powder was prepared by sufficiently mixing EA209 and 10% by weight sulfanilic acid-bearing dry granular activated carbon. The first and second mixed powders were weighed in a weight ratio of 1:1 and fully mixed in a small hoop shaker. The resulting mixed powder was then spread at a density of 240 g/m$^2$, and an adsorption sheet was prepared similarly to Example 1. The resulting sheet had satisfactory characteristics.

The sheet was shaped into a filter unit and examined for an actual effect as shown below. In a reciprocal pleating machine, the adsorption sheet of Example 1 was worked into a pleated filter unit with a filter thickness of 30 mm, a ridge-to-ridge pleat pitch of 6 mm and a filter front size of 200 mm×200 mm. As a result, it has been found that no cracking occurs at the ridge portions in the pleated structure and that the resulting filter is robust. It has also been found that a face velocity of 4 m/s applied from the Sheet A side causes no ridge crushing and that the sheet has excellent workability and handleability. To be further examined for an actual effect, the adsorption sheet was attached to an end face-fixing frame to form a unit, which was then placed in a car air conditioner. The air conditioner was operated in the outside air-introducing mode at a face velocity of about 1 m/s in a steady state (AUTO). The heating-cooling power hardly changed from that at the time when the filter was not installed. All the passengers (four monitors) in the car followed 10 m behind a diesel car and did not notice any unpleasant odor specific to diesel exhaust gas.

Some contents and test results of the examples and the comparative examples are summarized in Table 1.

TABLE 1

| | Activated Carbon | | | Powdered Thermoplastic Resin | | | | | |
|---|---|---|---|---|---|---|---|---|---|
| | Type | Particle Diameter (μm) | Amount (g/m$^2$) | Type | Average Particle Diameter (μm) | MI (g/10 min) | Amount (G/m$^2$) | Sufficient Powder-Mixing | Base Sheet |
| Example 1 | Coal | 300 | 220 | Ethylene-Acrylic Acid Copolymer | 10 | 9 | 22 | Yes | A: Bulky Sheet |
| Comparative Example 1 | Coal | 300 | 220 | Ethylene-Acrylic Acid Copolymer | 10 | 9 | 22 | No | A: Bulky Sheet |
| Comparative Example 2 | Coal | 300 | 220 | Ethylene-Acrylic Acid Copolymer | 10 | 9 | 22 | Yes | B: Non-Bulky Sheet |
| Example 2 | Coal | 300 | 220 | Poly-ethylene (LDPE) | 12 | 70 | 22 | Yes | A: Bulky Sheet |
| Example 3 | Coal | 300 | 220 | Poly-ethylene (LDPE) | 30 | 24 | 30 | Yes | A: Bulky Sheet |
| Example 4 | Coal | 300 | 220 | Poly-ethylene (HDPE) | 12 | 40 | 22 | Yes | A: Bulky Sheet |
| Example 5 | Coal | 300 | 220 | Polyester | 35 | 78 | 22 | Yes | A: Bulky Sheet |
| Example 6 | Coal | 200 | 120 | Ethylene-Acrylic Acid Copolymer | 10 | 9 | 12 | Yes | A: Bulky Sheet |
| Example 7 | Coal | 500 | 440 | Ethylene-Acrylic Acid copolymer | 10 | 9 | 45 | Yes | A: Bulky Sheet |
| Example 8 | Poly-ethylene-imine-Bearing Activated carbon | 300 | 220 | Ethylene-Acrylic Acid Copolymer | 10 | 9 | 45 | Yes | A1: Citric Acid-Bearing Bulky Sheet |
| Example 9 | Poly-ethylene-imine-Bearing Activated carbon | 300 | 110 | Ethylene-Acrylic Acid Copolymer | 10 | 9 | 45 | Yes | A1: Citric Acid-Bearing Bulky Sheet |
| | Sulfanilic Acid-Bearing Activated Carbon | | 110 | | | | | | |

TABLE 1-continued

| | Air-permeable Sheet | Adhesion Property | Thickness (mm) | Air-Flow Resistance (Pa) | Dust Holding Capacity (g/m²) | Toluene-Adsorbing Performance by One Pass (%) | Remarks |
|---|---|---|---|---|---|---|---|
| Example 1 | B: Non-Bulky Sheet | ○ | 0.8 | 20 | 42 | 75 | More uniform sheet prepared by a process including the step of preheating with infrared radiation |
| comparative Example 1 | B: Non-Bulky Sheet | X | 0.9 | 35 | 38 | 73 | |
| comparative Example 2 | B: Non-Bulky Sheet | ○ | 0.7 | 50 | 23 | 75 | |
| Example 2 | B: Non-Bulky Sheet | ○ | 0.8 | 20 | 41 | 73 | |
| Example 3 | B: Non-Bulky Sheet | ○ | 0.8 | 22 | 40 | 73 | |
| Example 4 | B: Non-Bulky Sheet | ○ | 0.8 | 20 | 42 | 74 | |
| Example 5 | B: Non-Bulky Sheet | ○ | 0.8 | 20 | 42 | 74 | |
| Example 6 | B: Non-Bulky Sheet | ○ | 0.6 | 20 | 45 | 73 | |
| Example 7 | B: Non-Bulky Sheet | ○ | 1.4 | 60 | 33 | 95 | |
| Example 8 | B: Non-Bulky Sheet | ○ | 0.8 | 20 | 42 | 73 | Deodorant Efficiency by One Pass Aldehyde: 50% Ammonia: 60% |
| Example 9 | B: Non-Bulky Sheet | ○ | 0.8 | 20 | 42 | 73 | Deodorant Efficiency by One Pass Aldehyde: 48% Ammonia: 70% |

Industrial Applicability

As described above, the adsorption sheet and the air-purifying filter according to the invention can not only have a very low air-flow resistance, good adhesion properties and a good deodorizing performance but also be resistant to clogging by dust. In addition, the inventive sheet can be easily pleated and can be relatively thin, so that the ridge-to-ridge pleat pitch can be small and that the pleated sheet can form a filter unit having a larger working area. Such a filter unit can be excellent with respect to air-flow resistance, dust holding capacity, deodorizing performance, and any other characteristics. Such characteristics can be obtained by a more simple manufacturing method, in comparison with the conventional technique. Thus, the industrial applicability of the invention is significant.

What is claimed is:

1. An adsorption sheet, comprising a structure formed by a process comprising:
   spreading a mixed powder on a base sheet, wherein the mixed powder is a product of premixing a powdered adsorbent and a powdered thermoplastic resin having a melt index of 0.1 to 80 g/10 minutes; and then
   pressing the mixed powder-containing base sheet at a temperature equal to or higher than a melting point of the powdered thermoplastic resin to form the adsorption sheet, wherein the base sheet has a fiber packing density of 0.15 g/cc or less.

2. The adsorption sheet according to claim 1, wherein the powdered thermoplastic resin has an average particle diameter of 1 to 40 μm.

3. The adsorption sheet according to claim 1 or 2, wherein the mixed powder has a weight ratio of the powdered thermoplastic resin to the powdered adsorbent of 1 to 40% by weight.

4. The adsorption sheet according to claim 1 or 2, wherein in a dust supply test using a JIS powder type No. 15, the adsorption sheet with the base sheet surface facing upstream holds 30 g/m² or more of the powder by the time when its air-flow resistance increases from the initial value by 150 Pa under the conditions of a linear velocity of 30 cm/second and a dust concentration of 0.5 g/m³.

5. The adsorption sheet according to claim 1 or 2, wherein the process for forming the structure further comprises holding an agent on the powdered adsorbent and holding another, different agent on the base sheet and/or an air-permeable sheet.

6. The adsorption sheet according to claim 1 or 2, wherein the powdered thermoplastic resin is at least on resin selected from the group consisting of polyolefins, polyamides, polyurethanes, polyesters, an ethylene-acryl copolymer, polyacrylate, polyarene, polyacryl, polydiene, an ethylene-vinyl acetate copolymer, PVC, and PS.

7. A laminate structure comprising the adsorption sheet according to claim 1 or 2 comprising the mixed powder of the powdered adsorbent and the powdered thermoplastic resin; and a laminated air-permeable sheet, wherein the mixed powder is placed between the base sheet and the air-permeable sheet.

8. An air-purifying filter comprising the laminate structure according to claim 7.

* * * * *